United States Patent [19]
Mason et al.

[11] Patent Number: 5,316,250
[45] Date of Patent: May 31, 1994

[54] FLUID CONTAINER STAND FOR THERAPEUTIC TREATMENTS

[75] Inventors: Bradley R. Mason, Olivehain; Jeffrey T. Mason, Escondido, both of Calif.

[73] Assignee: Breg, Inc., Vista, Calif.

[21] Appl. No.: 937,597

[22] Filed: Aug. 31, 1992

Related U.S. Application Data

[63] Continuation-in-part of Ser. No. 906,407, Jul. 1, 1992.

[51] Int. Cl.$^5$ .............................................. F16M 13/00
[52] U.S. Cl. ..................................... 248/165; 249/150
[58] Field of Search ............ 248/150, 165, 146, 163.1, 248/430, 431

[56] References Cited

U.S. PATENT DOCUMENTS

| | | | |
|---|---|---|---|
| 4,245,808 | 1/1981 | John | 248/165 X |
| 4,634,090 | 1/1987 | Corrie et al. | 248/165 X |

Primary Examiner—Douglas D. Watts
Attorney, Agent, or Firm—Rodney F. Brown

[57] ABSTRACT

A fluid container stand is provided having an extension member supported in an upright vertical position by an underlying base. The base is constructed from a plurality of planar base members and a plurality of planar union members. The base members are radially disposed about the longitudinal axis of the stand in an upright intersecting position and provide a slot at their top ends to receive the lower end of the extension member. The union members orthogonally engage the base members at predetermined vertical intervals along the longitudinal axis of the stand to securely maintain the base members in their desired position. The stand is further provided with a hooked structure mounted on the upper end of the extension member for suspending fluid containers therefrom.

18 Claims, 2 Drawing Sheets

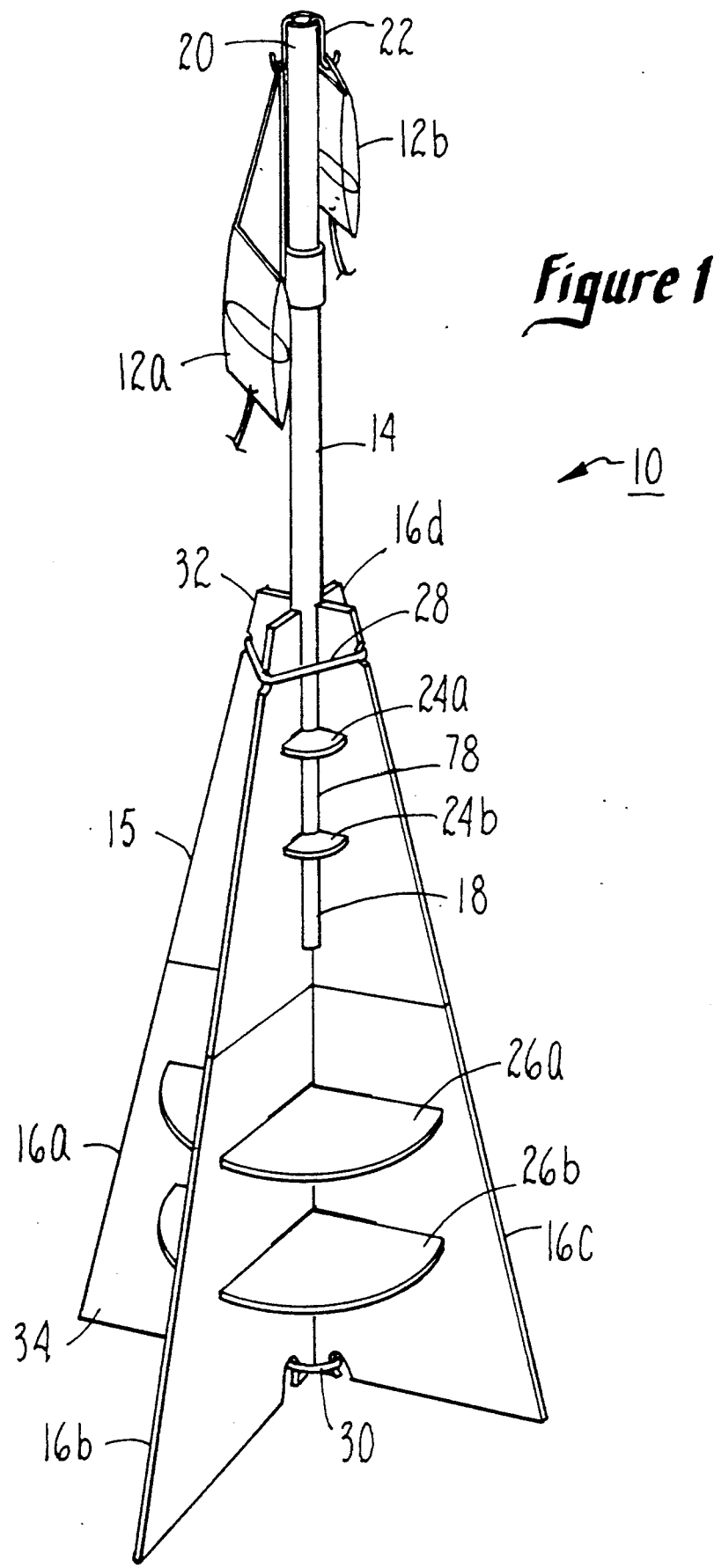

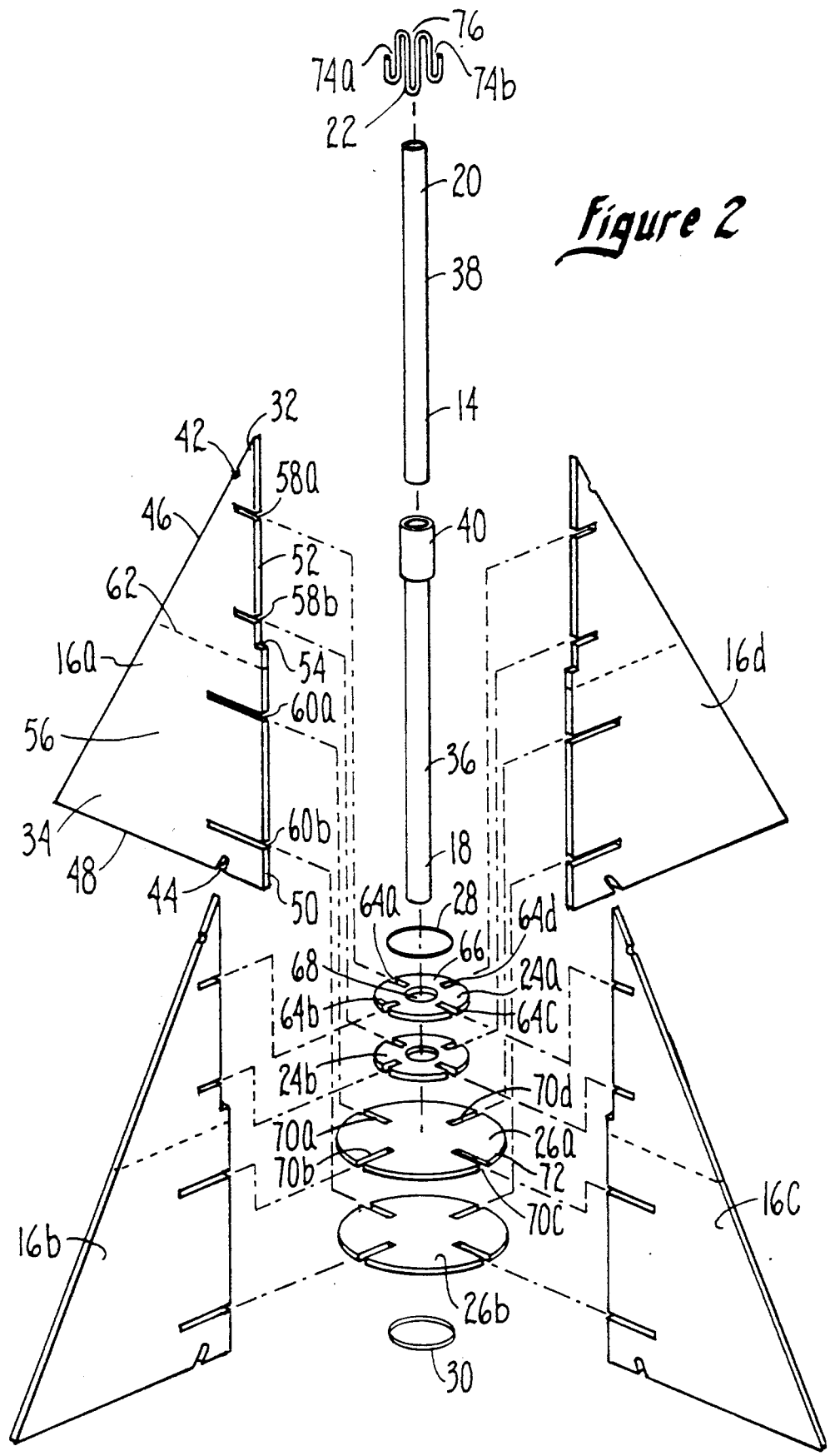

FLUID CONTAINER STAND FOR THERAPEUTIC TREATMENTS

This application is continuation-in-part patent application of our prior co-pending patent application entitled, "Gravity Driven Therapeutic Fluid Circulation Device", Serial No. 07/906,407, filed on Jul. 1, 1992.

TECHNICAL FIELD

The present invention relates to a stand from which one or more containers of fluid can be suspended, and more particularly to a fluid container stand wherein the fluid is used in therapeutic treatments of the body.

BACKGROUND OF THE INVENTION

Fluid container stands are typically used in medical treatments for suspending intravenous (IV) fluid bags overhead so that the IV fluid may be fed under the force of gravity to a patient positioned below the bag. Conventional IV stands are usually constructed from heavyweight stainless steel to withstand the rigors of continuous everyday use for extended periods of time in hospitals or other care facilities. A need exists, however, for a fluid container stand for short-term uses, such as individual home care.

Accordingly, it is an object of the present invention to provide a fluid container stand that is sturdy and stable, yet is fabricated from relatively lightweight and inexpensive materials, thereby rendering the stand practical for individual home care. It is another object of the present invention to provide such a stand that is essentially disposable at the end of its useful lifetime. It is further an object of the present invention to provide a fluid container stand that is relatively easy to assemble and disassemble, thereby rendering the stand fully portable and convenient to store or transport.

SUMMARY OF THE INVENTION

The present invention is a fluid container stand fabricated from inexpensive lightweight components that are readily assembled or disassembled to enable portability of the stand. The stand comprises an elongated extension member supported by base formed from a plurality of base members. The extension member has an open-ended tubular construction and each base member has a triangular-shaped planar construction, widening from top to bottom. When the stand is assembled, its longitudinal axis coincides with that of the extension member.

The base members are radially disposed about the longitudinal axis of the stand with their inside edges intersecting one another along the axis in parallel alignment with the axis. Each base member has a longitudinal notch formed at the top end of its inside edge such that a central longitudinal slot is provided where the top ends intersect. The longitudinal slot is sized to receive the lower end of the extension member in close fitting relation therewith, enabling the base to securely support the extension member in an upright vertical position.

The stand further comprises a plurality of union members which engage the base members at predetermined vertical intervals along the longitudinal axis of the stand to securely maintain the base members in their upright intersecting alignment. The union members have a circular-shaped planar construction and are aligned concentric with the longitudinal axis of the stand substantially orthogonal to the base members.

Each union member has a plurality of circumferential slits formed therein, which extend interiorly from the circumferential edge of the union member. Each of the circumferential slits is sized to tightly receive a base member. Corresponding slits are also formed in the base members, each slit in the base member aligning with a circumferential slit in the union member and sized to tightly receive the union member. The union members and base members securely engage one another by means of their correspondingly slitted configuration.

The stand is further provided with a means for suspending fluid containers from the extension member. The suspension means is a hooked structure mounted in the open upper end of the extension member. The hooked structure has a wave configuration forming three u-shaped segments in succession. The central u-shaped segment is sized to fit securely within the open upper end of the extension member while the two outer u-shaped segments form the hooks that extend from opposite sides of the extension member. When the stand is being used, fluid containers are suspended from either or both of the hooks.

Finally, the stand is provided with a pair of elastic bands that compressively engage the base members and further retain them in alignment with one another. One elastic band is sized to engage a series of notches formed in the outside edges of the base members proximal their top ends. The other elastic band is sized to engage a series of notches formed in the bottom edges of the base members proximal the bottom ends thereof. When in place, the elastic bands effectively prevent inadvertent disassembly of the stand. The bands, however, are readily removable when disassembly of the stand is desired.

The present invention will be further understood, both as to its structure and operation, from the accompanying drawings, taken in conjunction with the accompanying description, in which similar reference characters refer to similar parts

BRIEF DESCRIPTION OF THE DRAWINGS

FIG. 1 is a perspective view of the assembled stand of the present invention having fluid containers suspended therefrom.

FIG. 2 is a exploded perspective view of the disassembled stand of the present invention.

DESCRIPTION OF PREFERRED EMBODIMENTS

Referring initially to Figure the fluid container stand of the present invention, generally designated 10, is shown in an assembled state having a pair of fluid containers 12a, 12b suspended therefrom. Fluid containers 12a, 12b preferably contain a therapeutic treatment fluid, such as a nonambient temperature liquid being circulated from one container to the other through a intervening pad (not shown) positioned on the body of a patient in the manner of our copending U.S. patent application Ser. No. 07/906,407, incorporated herein by reference.

Stand 10 comprises an extension member 14 supported in a substantially vertical upright position by a base 15 made up of four base members 16a, 16b, 16c, 16d. Each base member 16a, 16b, 16c, 16d has a substantially identical configuration and is radially disposed beneath the lower end 18 of extension member 14 at equidistant 90° intervals about the longitudinal axis of extension member 14 and stand 10. The upper end 20 of extension member 14 has a suspension means 22 mounted thereon from which fluid containers 12a, 12b are suspended.

Stand 10 further comprises two pairs of union members vertically spaced along the longitudinal axis of the stand 10. The first pair is upper union members 24a, 24b that are configured substantially identically to each other. The second pair is lower union members 26a, 26b, that are likewise substantially identically configured to each other. Each union member 24a, 24b, 26a, 26b orthogonally engages all four of the base members 16a, 16b, 16c, 16d to maintain them in their desired radially-spaced alignment for support of extension member 14. Upper union members 24a, 24b also engage extension member 14, whereas lower union members 26a, 26b do not.

In addition to the above-recited union members, a continuous upper band 28 and a continuous lower band 30 are further provided to secure the desired alignment of base members 16a, 16b, 16c, 16d. Bands 28, 30 compressively engage the top and bottom ends 32 and 34 of each base member 16a, 16b, 16c, 16d, respectively.

Details of the configuration of the stand components and their interrelation to one another are further described with reference to FIG. 2. Extension member 14 has a three-piece tubular construction including a lower section 36, an upper section 38, and a joint section 40. Extension member 14 is preferably fabricated entirely from a rigid high-strength, yet lightweight, plastic such as PVC.

Joint section 40 is fitted over one end of lower section 36 and permanently attached thereto by means such as gluing. Extension member 14 is assembled by removably sliding an end of upper section 38 into joint 40, thereby releasably connecting upper section 38 with lower section 36. Upper end 20 of assembled extension member 14 remains open to receive and retain suspension means 22 in a manner described hereafter.

All four base members 16a, 16b, 16c, 16d are identically configured. Accordingly, the description of base member 16a set forth hereafter applies likewise to remaining base members 16b, 16c, 16d. Base member 16a is planar and widens from top end 32 to bottom end 34 in a substantially triangular configuration. An upper arcuate notch 42 and a lower arcuate notch 44 are formed in the outside edge 46 and the bottom edge 48, respectively, of base member 16a at points proximal the inside edge 50. A longitudinal notch 52 is also formed in the inside edge 50 extending downwardly from top end 32 and terminating proximal the midpoint of inside edge 50 at shoulder 54.

Base member 16a has two pairs of slits formed therein which are spaced at vertical intervals along the length of inside edge 52 and which partially extend through planar face 56 in a direction substantially parallel to bottom edge 48. The first pair of slits is upper slits 58a, 58b, each having a depth that is sized to receive upper union members 24a, 24b, respectively. The second pair of slits is lower slits 60a, 60b, each having a depth greater than the depth of upper slits 58a, 58b that is sized to receive lower union members 26a, 26b, respectively.

A crease 62 is also formed in base member 16a proximal its midpoint, extending across the entire planar face 56 of base member 16a parallel to bottom edge 48 and slits 58a, 58b, 60a, 60b. Crease 62 enables folding of base member 16a for storage when the stand 10 is in a disassembled state, while not substantially diminishing the degree of support provided by base member 16a to extension member 14 when stand 10 is in an assembled state. Base member 16a is preferably fabricated from a substantially rigid lightweight, yet foldable, material such as corrugated cardboard.

Union members 24a, 24b, 26a, 26b likewise have a planar construction and are preferably fabricated from a substantially rigid, lightweight material such as corrugated cardboard. Union members 24a, 24b, 26a, 26b all have a substantially circular configuration. Upper union members 24a, 24b are configured identically to each other. Accordingly, the description of upper union member 24a set forth hereafter applies likewise to upper union member 24b.

Upper union member 24a is provided with four upper circumferential slits 64a, 64b, 64c, 64d radially spaced at equidistant 90° intervals around the circumferential edge 66 of upper union member 24a. Upper circumferential slits 64a, 64b, 64c, 64d partially extend interiorly toward a central opening 68 formed through upper union member 44a. Central opening 68 is sized to slidably receive the lower end 18 of extension member 14 therethrough.

Lower union members 26a, 26b are likewise configured identically to each other and, thus, the description of lower union member 26a set forth hereafter also applies to lower union member 26b. Lower union member 26a has a greater diameter than upper union member 24a, but is similarly provided with four lower circumferential slits 70a, 70b, 70c, 70d radially spaced at equidistant 90° intervals around its circumferential edge 72. Lower circumferential slits 70a, 70b, 70c, 70d partially extend interiorly toward the center of lower union member 26a to a depth substantially greater than the depth of upper circumferential slits 64a, 64b, 64c, 64d. The center of lower union member 26a is continuous across its face, lacking a central opening.

Upper band 28 is preferably formed from an elastomeric material and is sized to compressively fit over top ends 32 of base members 16a, 16b, 16c, 16d within upper arcuate notches 42 when stand 10 is in an assembled state. Lower band 30 is likewise preferably formed from an elastomeric material. It is, however, sized to compressively fit within lower arcuate notches 44.

As noted above, suspension means 22 is configured for mounting in the open upper end 20 of extension member 14. Suspension means 22 is a hooked structure preferably fabricated from a substantially rigid metal wire. Suspension means 22 is formed in a wave configuration having two outer u-shaped segments 74a, 74b on opposite ends thereof and a central u-shaped segment 76 therebetween. Central u-shaped segment 76 is sized to fit within open upper end 20 while gripping extension member 14 between the adjacent sides of segments 74a and 76 and between the adjacent sides of segments 74b and 76, respectively.

When in use, stand 10 is fully assembled as shown in FIG. 1. However, the stand is readily disassembled as shown in FIG. 2, when the stand is not in use, such as during storage or transportation thereof. The disassembled stand may be compactly packaged in a manner not shown, but described hereafter, to facilitate storage or transportation. Compact packaging of the stand is accomplished by folding planar base members 16a, 16b, 16c, 16d along creases 62 and stacking them atop with planar union members 24a, 24b, 26a, 26b. Extension member 14 is split into lower and upper sections 36, 38 and the sections 36, 38 are bundled together with upper and lower bands 28, 30.

To assemble stand 10 from its disassembled state, extension member 14 is assembled by sliding upper section 38 into joint section 40. Central u-shaped segment 76 of suspension means 22 is then inserted into the open upper end 20 of extension member 14. The base 15 for extension member 14 is assembled by aligning upper slits 58a, 58b formed in each base member 16a, 16b, 16c, 16d with corresponding upper circumferential slits 64a, 64b, 64c, 64d formed in each upper union member 24a, 24b. Similarly, lower slits 60a, 60b formed in each base member 16a, 16b, 16c, 16d are aligned with corresponding lower circumferential slits 70a, 70b, 70c, 70d formed in each lower union member 26a, 26b.

With the slits so aligned, base members 16a, 16b, 16c, 16d are drawn inwardly to the longitudinal axis of stand 10 such that their inside edges 50 intersect at the axis. Simultaneously therewith, slits 64a, 64b, 64c, 64d, 70a, 70b, 70c, 70d engage base members 16a, 16b, 16c, 16d, and slits 58a, 58b, 60a, 60b engage union members 24a, 24b, 26a, 26b, respectively. Assembly of the base 15 is completed by elastically stretching upper band 28 and placing it in upper arcuate notches 42. Similarly, lower band 30 is elastically stretched and placed in lower arcuate notches 44.

The longitudinal notches 52 formed in base members 16a, 16b, 16c, 16d, along with central openings 68 formed through upper union members 24a, 24b, provide a longitudinal slot 78 through base 15 when assembled, as shown in FIG. 1. The final assembly step of stand 10 is to insert the lower end 18 of extension member 14 into slot 78 and slide end 18 downward therein until it abuts shoulders 54. Stand 10 is, thus, fully assembled and may be used for the suspension of fluid containers therefrom, such as the type designated 12a and 12b in FIG. 1.

In general, stand 10 is useful for the suspension of any relatively lightweight fluid container having a fluid outlet hose extending therefrom. Stand 10 enables the feeding of fluid from the container under the force of gravity to a source positioned at a height below that of the container. In particular, stand 10 can be used to feed therapeutic treatment fluids, e.g. a heating fluid, a cooling fluid or an intravenous fluid, to a patient positioned below the container for medical treatment of the patient in a manner known to one skilled in the art.

It is to be understood that the particular fluid container stand as shown and disclosed herein is illustrative of presently preferred embodiments of the instant invention. Other embodiments are, however, possible within the scope of the instant invention as disclosed and claimed herein.

We claim:

1. A fluid container stand comprising:
   an extension member having an upper end, a lower end, and a longitudinal axis;
   a plurality of planar base members, each of said base members having a bottom end and a top end, said plurality of base members radially disposed about said longitudinal axis of said extension member and engaging said lower end of said extension member; and
   a substantially planar union member engaging said plurality of base members.

2. A fluid container stand as recited in claim wherein each of said base members has a planar alignment substantially parallel to said longitudinal axis of said extension member.

3. A fluid container stand as recited in claim 1 wherein each of said base members widens from said top end to said bottom end.

4. A fluid container stand as recited in claim 3 wherein each of said base members is substantially triangular shaped.

5. A fluid container stand as recited in claim 1 wherein each of said base members has a longitudinal notch formed in said top end to provide a slot between said plurality of base members sized to retain said lower end of said extension member.

6. A fluid container stand as recited in claim 1 wherein said union member is aligned substantially orthogonal to said plurality of base members.

7. A fluid container stand as recited in claim 1 wherein said union member has a plurality of slits formed therein, each of said slits receiving one of said base members.

8. A fluid container stand as recited in claim 7 wherein each of said base members has a corresponding slit formed therein to receive said union member.

9. A fluid container stand as recited in claim 1 further comprising a plurality of said union members vertically spaced apart and engaging said plurality of planar base members.

10. A fluid container stand as recited in claim 1 further comprising means for suspending a fluid container from said extension member.

11. A fluid container stand as recited in claim 10 wherein said suspension means comprises a hook mounted on said upper end of said extension member.

12. A fluid container stand as recited in claim 10 wherein said extension member is an elongated tube with said upper end open to receive said suspension means therein.

13. A fluid container stand comprising:
    an extension member having an upper end, a lower end, and a longitudinal axis;
    a plurality of planar base members, each of said base members having a bottom end and a top end, said plurality of base members radially disposed about said longitudinal axis of said extension member and engaging said lower end of said extension member; and
    an elastic band engaging said plurality of base members and retaining said plurality of base members in alignment with one another.

14. A fluid container stand comprising:
    an extension member having an upper end, a lower end, and a longitudinal axis;
    a plurality of planar base members, each of said base members having a bottom end, a top end, and a longitudinal notch formed in said top end, said plurality of base members radially disposed about said longitudinal axis of said extension member such that said longitudinal notches form a slot retaining said lower end of said extension member; and
    a planar union member aligned substantially orthogonal to said plurality of base members and engaging said plurality of base members.

15. A fluid container stand as recited in claim 14 wherein said union member has a plurality of slits formed therein, each of said slits receiving one of said base members.

16. A fluid container stand as recited in claim 15 wherein each of said base members has a corresponding slit formed therein to receive said union member.

17. A fluid container stand as recited in claim 14 further comprising a hooked structure with a continuous wave configuration having two hooks positioned on opposite ends of said structure and a central u-shaped segment positioned between said hooks, wherein said extension member is an elongated tube with said upper end open and said central u-shaped segment is mounted within said open upper end such that said hooks extend radially from said upper end of said extension member.

18. A fluid container stand comprising:
   an extension member having an upper end, a lower end, and a longitudinal axis;
   a plurality of planar base members, each of said base members having a bottom end, a top end, and a longitudinal notch formed in said top end, said plurality of base members radially disposed about said longitudinal axis of said extension member such that said longitudinal notches form a slot retaining said lower end of said extension member;
   a planar union member aligned substantially orthogonal to said plurality of base members and engaging said plurality of base members;
   a plurality of slits formed in said union member, each of said slits receiving one of said base members; and
   a corresponding slit formed in each of said base members to receive said union member.

* * * * *